United States Patent

McLees

[11] Patent Number: 5,183,468
[45] Date of Patent: Feb. 2, 1993

[54] SNAP RING NEEDLE GUARD

[76] Inventor: Donald J. McLees, 2623 Virginia Ave., Everett, Wash. 98201

[21] Appl. No.: 679,561

[22] Filed: Apr. 2, 1991

[51] Int. Cl.⁵ .......................................... A61M 5/178
[52] U.S. Cl. ................................... 604/164; 604/110; 604/198; 128/919
[58] Field of Search ............... 604/110, 162, 164, 166, 604/168, 192, 198, 197, 265; 128/919

[56] References Cited

U.S. PATENT DOCUMENTS

| | | | |
|---|---|---|---|
| 4,795,432 | 1/1989 | Karczmer | 604/110 |
| 4,846,811 | 7/1989 | Vanderhoof | 604/263 |
| 4,917,672 | 4/1990 | Terndrup et al. | 604/192 |
| 4,929,241 | 5/1990 | Kulli | 604/263 |
| 4,935,013 | 6/1990 | Haber et al. | 604/192 |
| 4,952,207 | 8/1990 | Lemieux | 604/164 |
| 4,964,854 | 10/1990 | Luther | 604/166 |
| 4,973,317 | 11/1990 | Bobrove | 604/198 |
| 4,994,041 | 2/1991 | Dombrowski et al. | 604/164 |
| 4,995,866 | 9/1991 | Corey | 604/192 |
| 5,013,305 | 5/1991 | Opie et al. | 604/192 |
| 5,051,109 | 9/1991 | Simon | 604/263 |
| 5,051,109 | 9/1991 | Simon | 604/263 |
| 5,059,180 | 10/1991 | McLees | 604/110 |
| 5,085,648 | 2/1992 | Purdy et al. | 604/198 |
| 5,098,389 | 3/1992 | Cappucci | 604/158 |

FOREIGN PATENT DOCUMENTS 9101151 2/1991 World Int. Prop. O. .......... 604/164

Primary Examiner—C. Fred Rosenbaum
Assistant Examiner—Mark O. Polutta

[57] ABSTRACT

A guard (6) for the tip of a catheter insertion needle (5) which resides initially inside the standard catheter hub (3) and becomes automatically locked onto the tip of the standard insertion needle when the needle is withdrawn from the catheter. A small internal pivoting lever (8) sensitive to the end of the needle closes the internal teeth (12) of a snap ring (7) onto the needle (5) to hold the guard (6) in one direction while the one way lever prevents the needle tip from exiting the guard in the other direction.

7 Claims, 6 Drawing Sheets

SNAP RING NEEDLE GUARD

BACKGROUND OF THE INVENTION

1. Field of the Invention

This invention relates to medical instruments. It applies to medical needles in general and specifically to the needles used for placing an intravenous catheter into a vein, although it can also be applied to other hypodermic needles. In the U.S. Patent Office it would be found in a classification for needle tip guards which protect health care workers from accidental needle sticks.

2. Description of the Prior Art

At this time the need for needle guards which protect health care workers from exposure to AIDS and hepatitis and the like through accidental needle sticks has been well established. A multitude of these protection devices exist in the prior art and some have made their way to the market place.

Many of the devices of the prior art apply specifically to intravenous catheter insertion kits. Such a kit is generally comprised at least in part of an insertion needle inside a flexible catheter which in turn is attached to a standard fluid fitting, usually referred to as a hub. In operation the insertion needle and surrounding catheter together enter the patient's vein. The needle is then removed leaving the catheter in place inside the vein. Fluid lines for administering medications or nutrients can then be attached to the hub through a standard Luer lock or other convenient means and the fluids can then be fed though the catheter directly into the blood vessel.

The problem the devices of the prior art attempt to solve is how to protect health care workers from the sharp point of the insertion needle which has been exposed to possibly contaminated blood. This applies to personnel who must dispose of the needle as well as those who must manipulate the needle at withdrawal, and is of special concern during emergency situations when care must be administered quickly to patients of unknown health status using possibly inadequate disposal facilities. For example, many I.V.s must be administered at the site of an accident.

Several prior art inventions solve the problem by offering kits which retain the needle inside the medication administering system or allow the needle to be retracted back up inside the insertion apparatus and then discarded. Both Wanderer et al., U.S. Pat. No. 4,850,961 (1989) and Braginetz et al., U.S. Pat. No. 4,932,945 (June 1990) describe intravenous catheter insertion devices which include an insertion handle or housing that provide for retracting the needle inside the housing after the catheter has been inserted, thus allowing disposal of the entire insertion kit less the catheter. These devices are necessarily relatively bulky and therefore would be more difficult to manipulate relative to a simple insertion needle. They are also quite complex and would require a complete re-design of standard placement systems, resulting in a substantial increase in cost. Also, the user is obliged to perform more complex actions than with a simple insertion needle.

An invention by Jagger et al., U.S. Pat. No. 4,781,692 (1988) is different in that the insertion needle is withdrawn from the catheter but remains in a sealed housing and flexible tube to which the intravenous fluid lines are then attached. Such an approach, besides introducing increased complexity and increased costs also presents increased flow restriction with a sharp rigid needle inside a bulky housing which must remain attached to the patient's arm or other appendage often for extended time periods, resulting in increased discomfort at best and allowing a possibly dangerous situation to exist.

Ideally an intravenous needle guard should be entirely automatic in that the act of withdrawing the needle from the catheter causes the guard to become activated, therefore requiring no additional responsibilities or actions from the health care worker beyond those required by a standard insertion kit. In addition it should be quite simple and inexpensive, requiring the very minimum of insertion kit re-design. Such a device becomes possible if the guard were intended to enclose only the sharp tip instead of the entire needle.

One embodiment of an invention by Vaillancourt, U.S. Pat. No. 4,725,267 (1988) is a hypodermic needle tip guard, but it has no provision to be automatically activated when used in conjunction with an intravenous insertion kit and has no provision for resisting being pulled off the tip other than the slight pull offered by a small coil spring.

The same is true of a tip guard by Martin, U.S. Pat. No. 4,887,998 (1989), although it does additionally provide a small occluding ball to positively prevent penetration of the guard by the enclosed tip.

A hypodermic needle tip guard invented by Kulli, U.S. Pat. No. 4,929,241 (1990), likewise is not intended for automatic activation by intravenous insertion needle withdrawal and therefore has no provision for such, but it does have internal blades intended to grasp the needle tip when it becomes enclosed by the guard and therefore resists efforts to be pulled from the tip. Conceptually this approach offers a simple functional tip guard but practically speaking would fall short of an ideal guard if modified for IV needles.

Ideally such a guard would reside initially in available space inside the catheter hub until the needle is withdrawn, at which time it would close upon the tip. If the Kulli guard were miniaturized and placed inside the catheter hub the clamping force would not be sufficient. If placed over the needle outside the hub, complete re-design of the insertion kit would be required and usage would be made more difficult.

Tip guards of the Kulli type use the presence of the needle tip to oppose the clamping force. A substantial spring force is required for the clamping means to dig into the steel needle surface. The force is released when the tip enters the guard, so there would be significant additional drag on the needle as it is withdrawn from the catheter if this type of guard were used with an insertion kit.

A needle tip guard invented by Lemieux, U.S. Pat. No. 4,952,207 (1990) is specifically intended for usage with an I.V. insertion kit and it avoids high withdrawal drag by not needing high spring pressure to grasp the needle. It does, however, require that the end of the needle be modified by the addition of a slot on the side which allows the guard to capture the tip. In anticipation of a possible problem created by the slot, that of an unwanted flow of blood emanating from the slot and flowing between the inner surface of the catheter and the outer surface of the needle, the Lemieux specification proposes an additional thin membrane over the slot which would prevent leakage yet be flexible enough to still allow the guard to capture the tip. Such additional complexities are not desirable. The ideal needle tip guard from the standpoint of I.V. insertion kit manufacturers would be one that doesn't require any modification of existing needles.

In reviewing the prior art it becomes evident that one simple I.V. needle guard which satisfies all significant requirements from both the point of view of the users and the manufacturers does not yet exist.

SUMMARY OF THE INVENTION

This invention is a guard for an intravenous catheter insertion needle which automatically captures the needle tip when the insertion needle is withdrawn from the catheter and its attached hub. Thus no additional action whatsoever is required of the user to activate the guard beyond that normally required to insert a catheter into a patient's blood vessel and then remove the needle. While the primary intent is to use this guard in conjunction with an I.V. insertion kit, it could also be used as a manually activated tip guard for any hypodermic needle.

In order to satisfy the objectives of extreme simplicity, low cost, and small size so that the guard can reside initially entirely inside the catheter hub in a currently existing available space, the invention consists of only three parts—a hollow housing, a retaining ring, and a lever. The lever need be no more than a short straight length of small sized bar stock.

The retaining ring serves as the grasping element. While this is not the usual way that a retaining ring would be used, for this application it is ideal. The ring can provide a very large grasping force or "squeeze" in a very small volume. Squeeze can be increased to any reasonable amount required by simply making the ring thicker or by using more rings.

Retaining rings, often referred to as "snap rings," are generally classified as either external or internal. The external variety, which includes the ring of this invention usually have a slit or gap which allows them to be expanded and then slid over a structural or mechanical member of circular cross section (a rod or shaft). In a typical application the ring is then allowed to contract into a groove on the member and thus retain the shaft or rod in a specific position relative to another element such as the shoulder of a housing through which the shaft passes. Often a special tool is required to expand the ring since the ring, usually made from high strength hardened steel, has considerable spring force in its expanded position. It is this spring force that this invention utilizes to grip the needle. Internal teeth dig into the surface of the needle when the ring is allowed to contract. Since a portion of the housing rearward of the ring tapers slightly inward, any attempt to pull the ring off the end of the needle results in more clamping pressure being applied to the needle through the teeth of the ring.

The only other part besides the housing is the lever, which serves multiple purposes. Initially it serves as a ring expander. Prior to needle withdrawal one end of the lever resides inside the retaining ring gap keeping the ends of the ring spread and the interior teeth expanded apart enough to allow the needle to slide freely. The other end of the lever rests against the needle and allows the lever to serve as a sensor of the needle tip. Since the ring gap tapers outward an outward directed portion of the ring spring force exerts pressure against the lever. The lever presses against a pivot point in the housing, but is kept from pivoting by the presence of the needle.

Since the outward component of the spring force on the lever is a function of the amount of outward taper of the ring gap, the ring can be designed such that the force of the other end of the lever against the needle is negligible, thus satisfying another objective of the invention. Even though the clamping force of the retaining ring can be quite substantial, negligible additional drag is transferred to the needle.

When the insertion needle is withdrawn from the catheter, the guard remains in place inside the catheter hub until the tip of the needle passes the distal end of the lever which is in contact with the needle surface. Passage of the needle past the distal end of the lever allows the retaining ring spring force at the gap to eject the proximal end of the lever as the distal end pivots into the path vacated by the needle and the snap ring closes on and grips the needle. With the guard mechanism firmly gripping the needle, further movement of the insertion needle out of the catheter and hub assembly also pulls the guard out.

When the insertion needle assembly is removed the needle tip is completely enclosed by the guard. Any attempt to pull the guard off results in the snap ring internal teeth gripping the needle even more. Another function of the lever, that of keeping the needle tip from coming back out of the guard once the mechanism has been triggered, is irreversible. The lever and snap ring gap are designed such that once the lever proximal end has been ejected and the gap closes, the lever cannot re-enter the gap. Thus any outside accidental force on the end of the guard regardless of magnitude would cause the needle to collapse before the tip can penetrate the guard.

BRIEF DESCRIPTION OF THE DRAWINGS

FIG. 4 is a side view cross section of the preferred embodiment of the guard and its internal mechanism in its non-activated state with the needle passing clear through.

Figure 8:
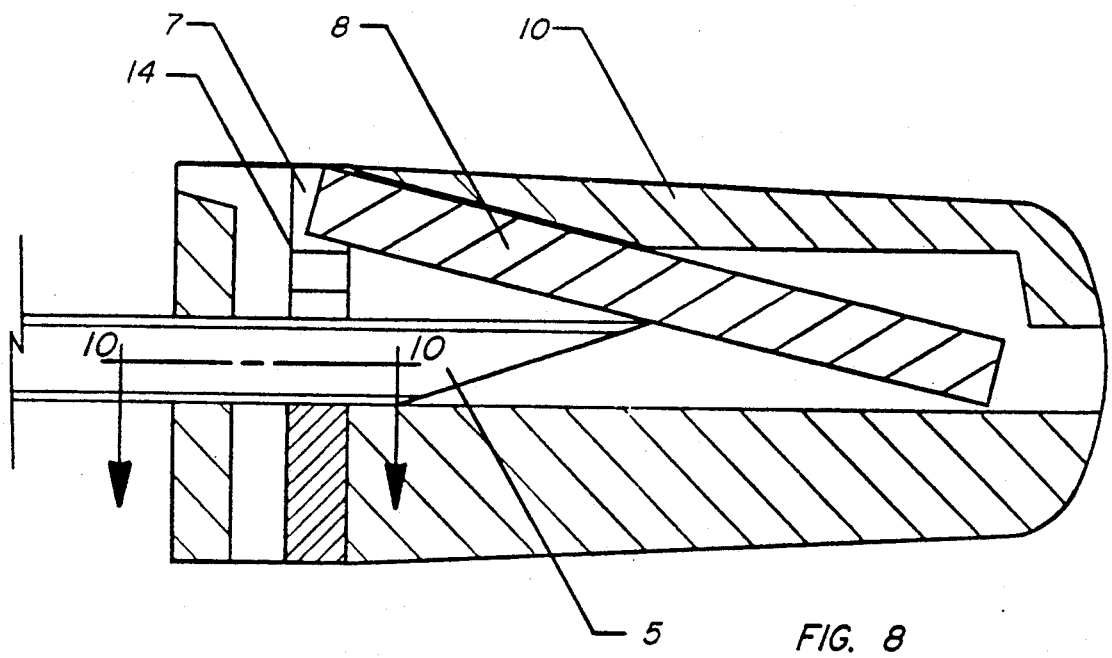

The FIG. 8 side view cross section shows the needle tip completely captured by the guard.

Figure 5:
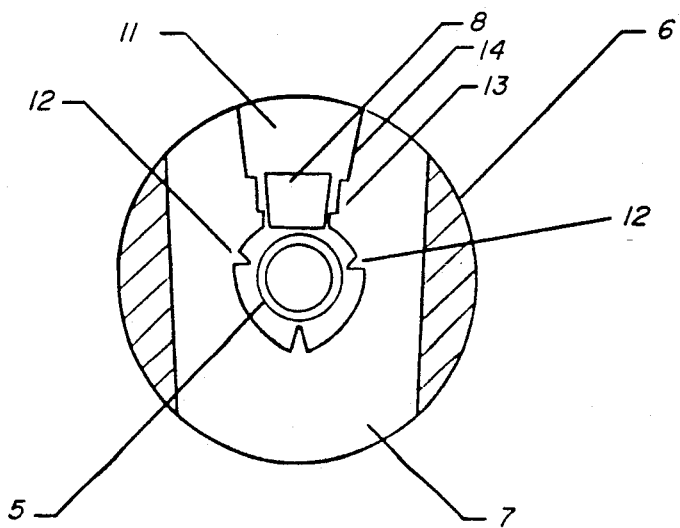
FIG. 5 is an end view cross section of the guard as shown in FIG. 4. The section line 5—5 of FIG. 4 shows the viewing point of the FIG. 5 view.
Figure 9:
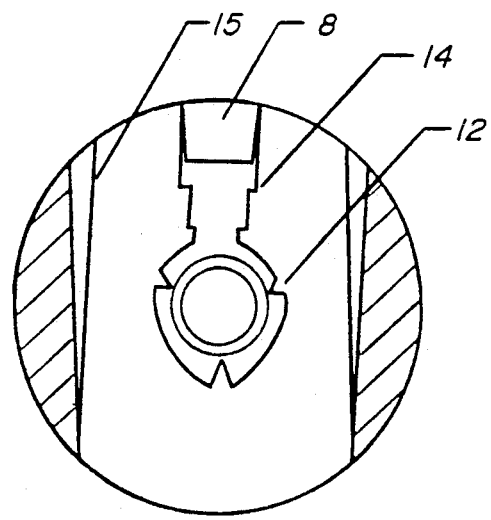

The end view cross section of FIG. 9 illustrates the fully actuated mechanism from the same viewing point as that of FIG. 5.

Figure 10:
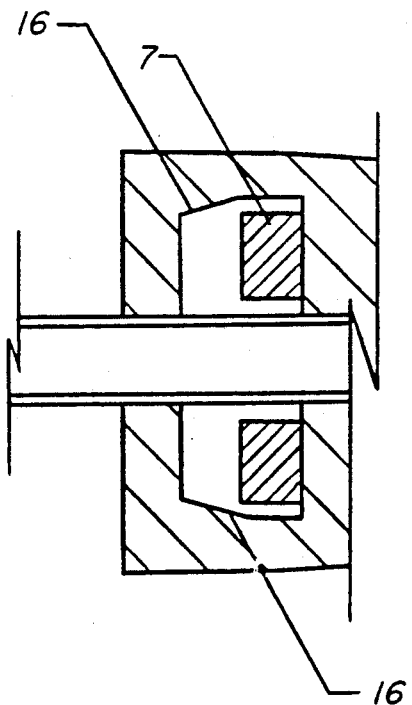

FIG. 10 is a partial top view cross section of the mechanism in the same state as that of FIG. 9. The point of view and direction is shown by section line 10—10 of FIG. 9.

Figure 11:
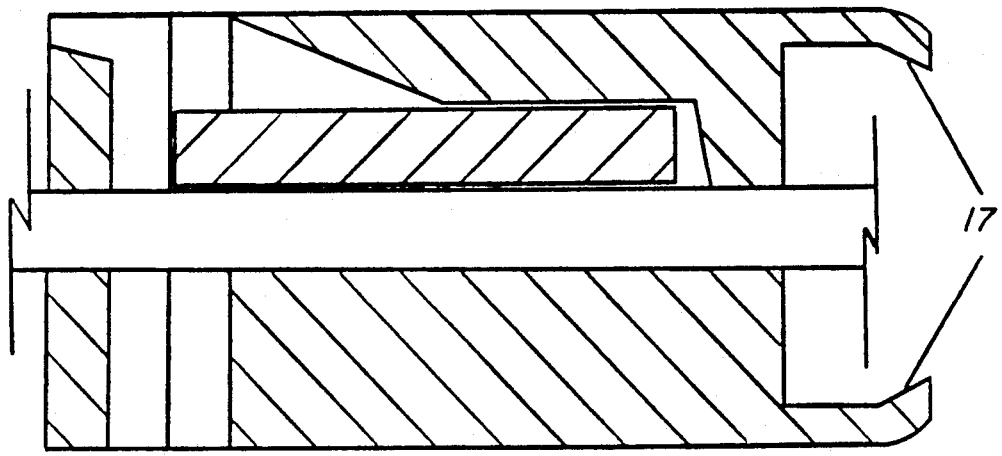

FIG. 11 illustrates an alternative preferred embodiment of the guard in side view cross section.

Figure 12:
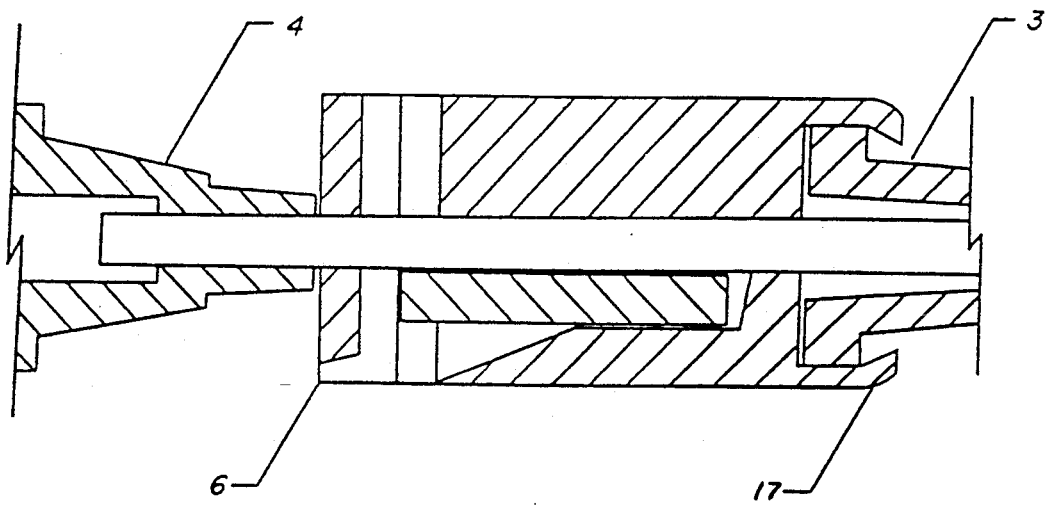

The alternative preferred embodiment is also shown in the side view cross section of FIG. 12 along with the other parts of the needle and catheter assembly.

Figure 13:
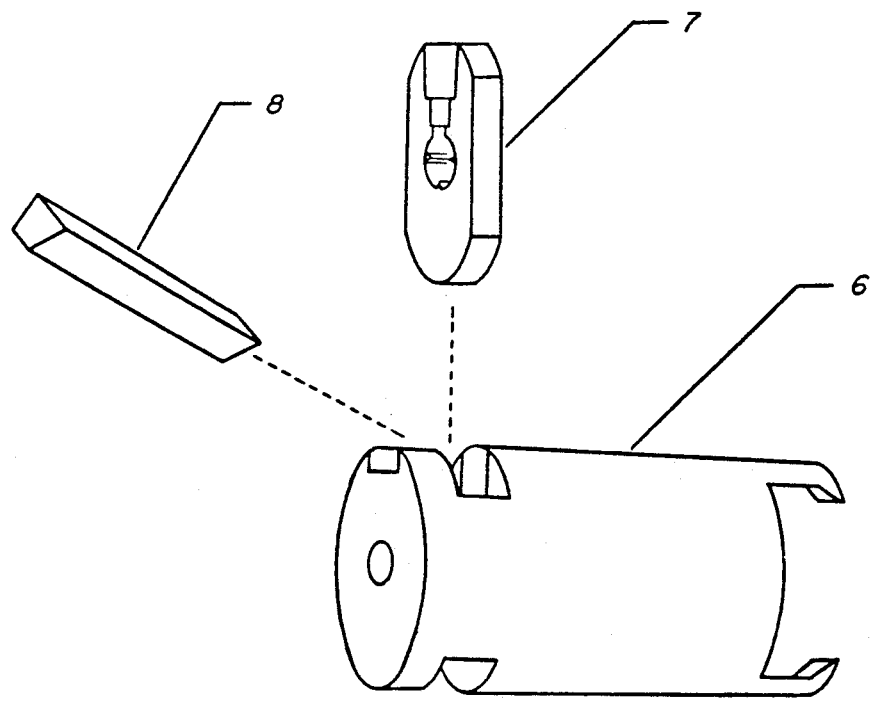

FIG. 13 is an exploded view in perspective showing the three parts of the needle guard.

DETAILED DESCRIPTION OF THE DRAWINGS

Figure 1:
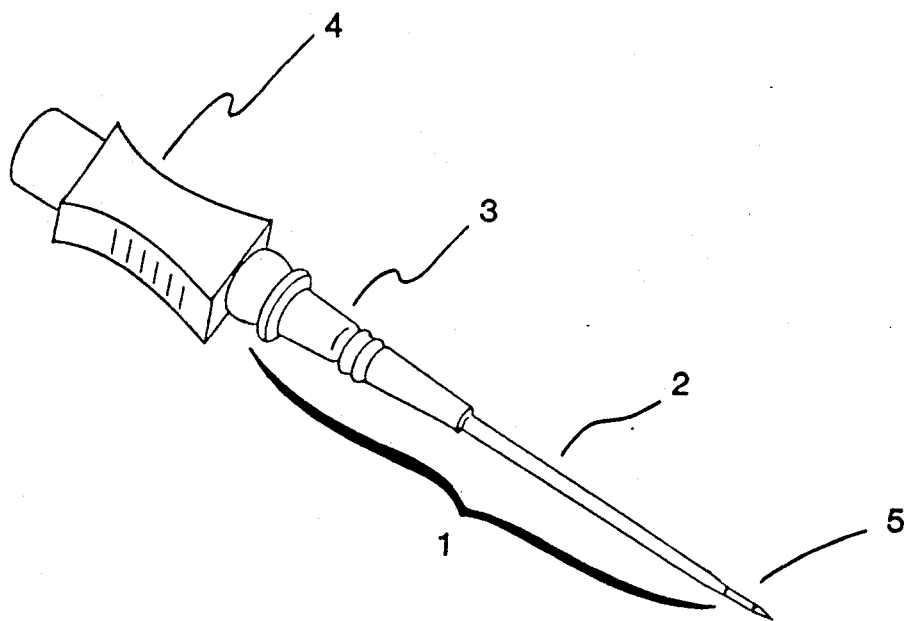
FIG. 1 is an isometric drawing showing a typical insertion needle, catheter, and hub assembly.

FIG. 1 illustrates a typical intravenous needle insertion assembly. The catheter assembly 1 is comprised of the flexible catheter 2 and its attached hub 3. The insertion handle 4 is generally made of a clear plastic, thus providing an internal flash chamber. The chamber allows blood to enter, thereby providing visual confirmation that the insertion needle has indeed entered a blood vessel. Attached to the handle is the insertion needle which passes through the catheter assembly. The tip of the needle 5 can be seen protruding from the end of the catheter 2.

Figure 2:
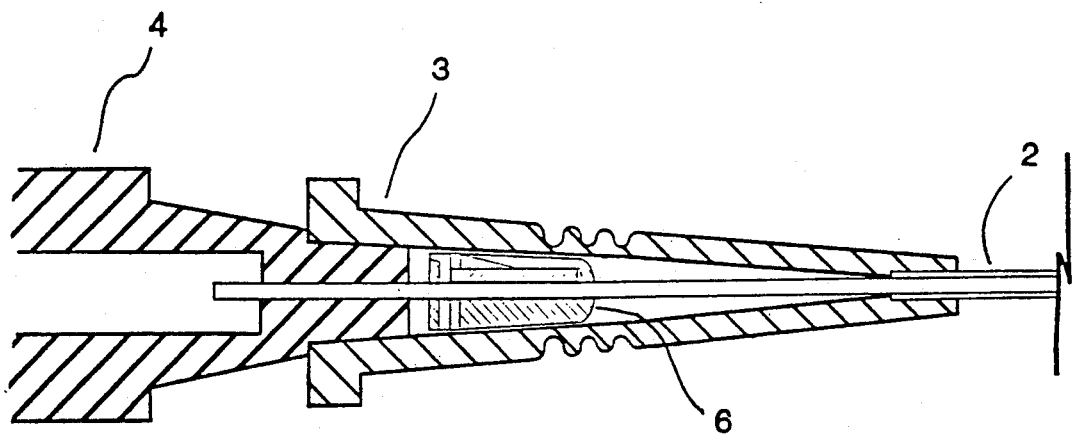
FIG. 2 is a side view cross section of an I.V. assembly and includes the guard inside the hub.

The guard 6 inside the hub 3 can be seen in the side view cross section of FIG. 2. At assembly the guard can be inserted into the hub at a depth sufficient for the force of friction between the guard and the hub to exceed the drag force of the needle passing through the guard and thereby hold the guard in place within the hub until the guard captures the needle tip.

Figure 3:
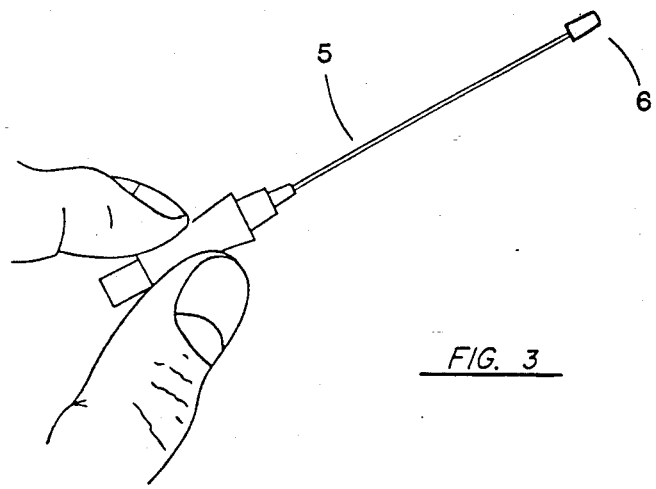
FIG. 3 is a prospective view illustrating the needle tip enclosed by the guard as it would appear after the needle has been pulled from the catheter and hub assembly.

Once the needle tip triggers the guard mechanism causing the snap ring to grab the needle, continuing removal of the needle from the catheter and hub will automatically pull the guard out as shown in FIG. 3. Thus the tip of the needle 5 has become protected by the guard 6 with no additional action required on the part of the operator beyond the normal insertion of the catheter and withdrawal of the needle.

Figure 4:
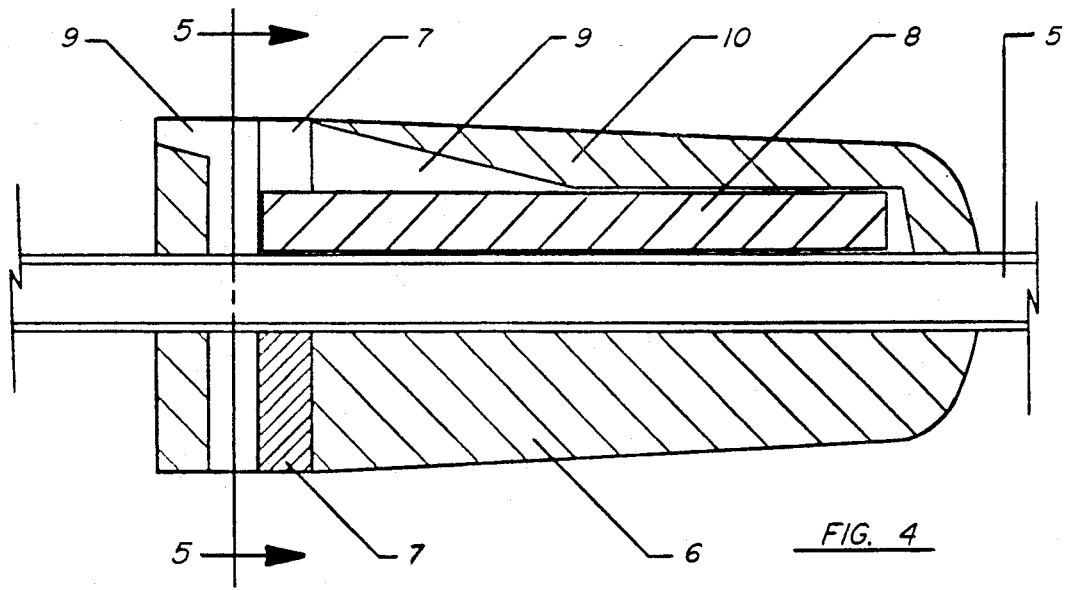

The internal workings of the guard mechanism can be seen in more detail in the side view cross section of FIG. 4. Here the tip of the needle 5 has not yet entered the guard 6, so the lever 8 keeps the snap ring 7 spread apart. The internal cavity 9 provides room for the mechanism to move and for easy insertion of the lever and snap ring at assembly. The outside opening of the internal cavity 9 can be designed such that while the lever can be easily forced into position at assembly, it cannot accidentally slide back out after the guard has been actuated.

In the end view cross section of FIG. 5 the entire snap ring 7 can be seen. The lever 8 is wedged between the shoulders at 13 keeping the ring gap 11 spread open and the internal teeth 12 of the snap ring spread apart enough so that the needle 5 can easily slide through. Part of the guard housing 6 alongside the ring 7 can be seen cross hatched.

Figure 6:
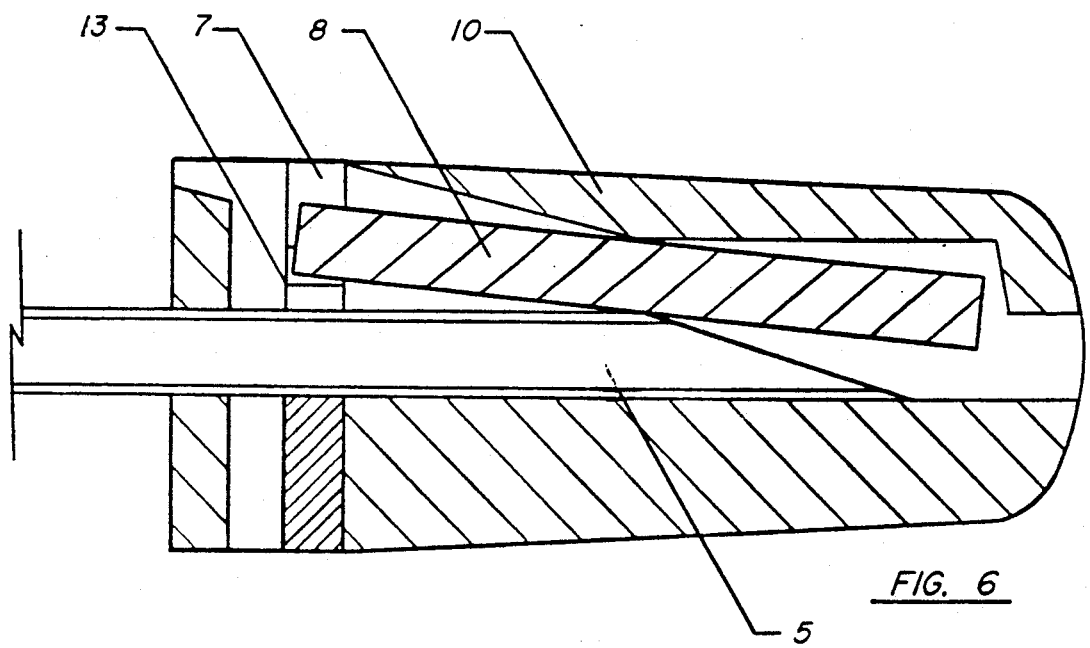
FIG. 6 is a side view cross section of the mechanism as it appears with the needle partially withdrawn into the guard.
Figure 7:
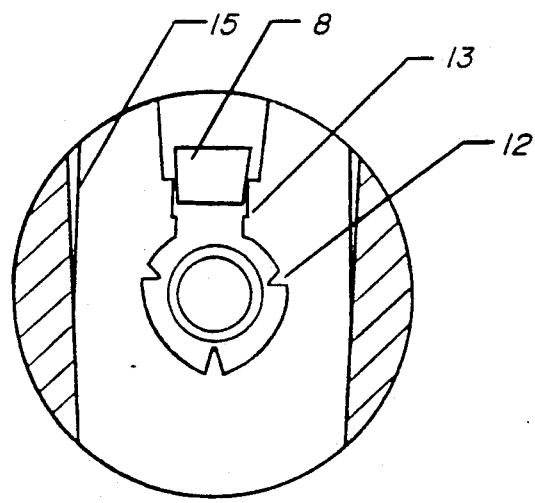
FIG. 7 is an end view cross section of the partially activated mechanism in the same state as that of FIG. 6 and from the same viewing point as that of FIG. 5.

In FIG. 6 the tip of the needle has entered the guard. In this particular case the very tip of the needle is on the bottom. Since the needle and handle are free to rotate relative to the guard and hub, the tip could just as well be on top. The shoulder at 13 of FIG. 6 and FIG. 7 provide for positive activation of the mechanism regardless of rotational position of the needle or slight variations in manufacturing tolerances. In the static state of the mechanism when the needle passes clear through the guard, the expanded snap ring is exerting an outward force on the end of the lever at the ring gap. The lever cannot move because the other end is against the needle. But when the bevel of the tip begins to move past the end of the lever as in FIG. 6, the end of the lever away from the snap ring (the distal end) is free to move into the area vacated by the needle as the lever pivots at the guard housing pivot point 10 and the gap end of the lever (the proximal end) is pushed by the spring force of the snap ring away from the needle and outside of the shoulder at 13. At this point there is no guarantee that the snap ring teeth 12 have yet dug into the needle, since there will be slight manufacturing variations between different needles and different snap rings, and because the exact place the teeth grab the needle will also be somewhat dependent upon the force and speed the particular health care worker employs in withdrawing the needle. But regardless of whether or not the teeth 12 of FIG. 7 have yet grabbed the needle, the shoulder of the snap ring at 13 prevents the gap end of the lever from returning and therefore re-spreading the ring. Since the gap end of the lever cannot return, neither can the opposite end. The return path of the needle is therefore blocked by the lever, and the only direction the needle can move is outward from the guard, or to the left in FIG. 6. But as the needle moves more leftward, the snap ring is allowed to push the lever farther out of the ring gap until eventually the lever is pushed past the shoulder at 14 in FIG. 8 and 9, and the teeth 12 dig into the needle, thereby causing the guard to capture the needle tip. The needle cannot escape from where it entered because it is blocked by the one way lever. Since the snap ring teeth bite into the needle surface, further pulling on the needle pulls the guard from the hub. The ring can be hardened during the manufacturing process to guarantee the ring teeth will dig into the surface of the softer needle steel.

The guard housing can be designed such that the expanded snap ring also slightly bulges out the sides of the housing (shown cross hatched in FIGS. 5, 7, and 9). Thus at assembly the guard can be forced snugly into the hub to guarantee it can't be pulled out prior to capturing the needle tip. But when the mechanism does become tripped by the needle tip and the snap ring closes on the needle as shown in FIGS. 7 and 9, the frictional hold of the guard with the interior of the hub becomes released by the contracting snap ring allowing the guard to be easily extracted by the withdrawing needle.

A further aid to assure capture of the needle by the guard and amplify the gripping force of the ring teeth can be designed into the guard housing as shown by FIG. 10. The section line 10—10 in FIG. 8 shows the direction of the FIG. 10 view, which is a top view partial cross section. Here can be seen inward slanting surfaces 16 of the guard housing rearward of the snap ring. After closing on the needle the contracted snap ring releases its grip on the sides of the guard housing as shown in FIG. 9 thereby allowing the needle tip to pull the snap ring rearward against the inward slanting surfaces 16 of FIG. 10. But the slanted surfaces put an even greater squeezing force on the sides of the snap ring causing the ring teeth to dig even deeper into the needle surface. So any partial hang-up of the guard as it exits the hub (such as from the needle being pulled out at an odd angle instead of straight back) is overcome by the added force from the slanted surfaces. The greater the pull, the more the ring teeth are forced to dig in. The same is true of any outside force directed towards removing the guard from the needle tip once the guard and needle have been extracted together from the hub. That is, if someone tries to pull off the guard, the slanted surfaces cause the snap ring teeth to grip even tighter. The lever is of such a size and can be made strong enough so that the needle would collapse back upon itself before being forced the other way out the end of the guard.

FIG. 11 shows a side view cross section of an alternative preferred embodiment of the invention. This version is larger (the needle hole remains basically the same) and is designed to be initially placed outside the hub between the needle handle (4 of FIG. 12) and the hub (3 of FIG. 12). FIG. 12 shows the initial position of the guard 6 within the assembly also in side view cross section. Since this variation is placed outside the hub and therefore cannot depend on a force fit to hold the guard in place until extracted by the needle, ears (17 of FIG. 11) are provided to grasp the flange of the hub. The ears can be provided with slanted interior surfaces as shown so that further withdrawal of the needle after the guard captures the tip causes the ears to spread apart and their hold on the hub flange is released allowing the catheter and hub to remain in place as the guarded needle is extracted.

This alternative embodiment is provided to allow a larger guard that avoids the close tolerances and miniaturized components of the in-the-hub version. The disadvantage is that while the smaller unit can be incorporated into existing catheter insertion kits with little or no modification to the existing parts required, the outside-the-hub version requires at least a longer needle and larger protective sheath which encloses the needle/catheter assembly prior to use. But perhaps more important the larger version may be more cumbersome or in other ways more troublesome to use. Thus this invention offers the alternative of the completely-in-the-hub tip guard which does not affect standard operation or construction.

It should also be noted that either version or an "in between" version could be used as a tip protector for any hypodermic needle independent of catheter insertion kits, i.e., as a tip guard for injection needles, blood drawing needles, etc. In these applications the guard would reside initially against the hub of the standard needle and would be manually slid over the tip after the needle is used.

FIG. 13 is an exploded view showing the three parts of the guard and their placement direction at assembly. The inside-the-hub version would appear the same except it would not have the hub engagement ears and the needle hole would appear larger relative to the guard.

What is claimed is:

1. A medical needle and a needle tip guard, said needle being attached proximally to a standard sized needle hub and having a distal pointed tip and a cylindrical surface and said needle tip guard comprising:
   a hollow housing through which said needle passes;
   an expandable retaining ring captured within said hollow housing and through which said needle passes, said retaining ring having a gap which increases in width with distance from the axis of said ring and said ring having gripping means capable of gripping said needle when said ring is in its contracted state; and
   a lever captured within said hollow housing and residing outside of said needle on the same side of said needle as said retaining ring gap, the proximal end of said lever spreading apart said retaining ring gap and said gap exerting a force on said lever proximal end directed away from the needle axis, said lever being in pivotal contact with a point of said housing, and the distal end of said lever being in contact with said cylindrical surface of said needle whereby passage of said needle tip beyond the contact point between said needle surface and said distal lever end in the proximal direction allows said retaining ring gap force to pivot said lever about its contact point with said housing and eject said lever proximal end out of said retaining ring gap, said retaining ring thereby becoming contracted and closing said retaining ring gripping means upon said needle surface.

2. The guard of claim 1 wherein said lever has a proximal end width greater than said retaining ring gap width at a point of said gap furthest from said retaining ring axis when said retaining ring is in its contracted state such that said lever is prevented from returning to a position within said gap once said retaining ring gap force has ejected said lever.

3. The guard of claim 1 in which said housing has an interior cavity having a dimension perpendicular to the needle axis which decreases from the width of said retaining ring to a smaller dimension with distance from said retaining ring in the direction proximal of said ring.

4. An intravenous catheter insertion kit and a needle tip guard comprising:
   a flexible catheter and its attached standard sized catheter hub;
   an insertion needle assembly, the insertion needle being initially located inside said catheter hub and said catheter, said needle also being attached proximally to a standard sized needle hub and having a distal pointed tip and a cylindrical surface;
   a hollow needle tip guard enclosed entirely within said catheter hub and through which said needle passes;
   an expandable retaining ring captured within said hollow housing and through which said needle passes, said retaining ring having a gap which increases in width with distance from the axis of said ring and said ring having gripping means capable of gripping said needle when said ring is in its contracted state; and
   a lever captured within said hollow housing and residing outside of said needle on the same side of said needle as said retaining ring gap, the proximal end of said lever spreading apart said retaining ring gap and said gap exerting a force on said lever proximal end directed away from the needle axis, said lever being in pivotal contact with a point of said housing, and the distal end of said lever being in contact with said cylindrical surface of said needle whereby passage of said needle tip beyond the contact point between said needle surface and said distal lever end in the proximal direction allows said retaining ring gap force to pivot said lever about its contact point with said housing and eject said lever proximal end out of said retaining ring gap, said retaining ring thereby becoming contracted and closing said retaining ring gripping means upon said needle surface.

5. The guard of claim 4 in which said guard has an interior cavity having a dimension perpendicular to the needle axis which decreases from the width of said retaining ring to a smaller dimension with distance from said retaining ring in the direction proximal of said ring.

6. The guard of claim 4 wherein said lever has a proximal end width greater than said retaining ring gap width at a point of said gap furthest from said retaining ring axis when said retaining ring is in its contracted state such that said lever is prevented from returning to a position within said gap once said retaining ring gap force has ejected said lever.

7. The guard and catheter hub of claim 4 in which said catheter hub retains said guard inside said catheter hub by friction fit means until said guard is forcibly pulled from said hub.

* * * * *